(12) United States Patent
Chai

(10) Patent No.: US 10,139,336 B2
(45) Date of Patent: Nov. 27, 2018

(54) APPARATUS FOR CABLE INSPECTION

(71) Applicant: AJOU UNIVERSITY INDUSTRY-ACADEMIC COOPERATION FOUNDATION, Suwon, Gyeonggi-do (KR)

(72) Inventor: Jang Bom Chai, Seoul (KR)

(73) Assignee: AJOU UNIVERSITY INDUSTRY COOPERATION FOUNDATION, Suwon (KR)

( * ) Notice: Subject to any disclaimer, the term of this patent is extended or adjusted under 35 U.S.C. 154(b) by 143 days.

(21) Appl. No.: 15/265,141

(22) Filed: Sep. 14, 2016

(65) Prior Publication Data

US 2017/0074778 A1    Mar. 16, 2017

(30) Foreign Application Priority Data

Sep. 14, 2015 (KR) .................. 10-2015-0129615

(51) Int. Cl.
  *G01N 17/00*  (2006.01)
  *G01R 31/08*  (2006.01)
  *G01R 31/02*  (2006.01)

(52) U.S. Cl.
  CPC ......... *G01N 17/004* (2013.01); *G01R 31/021* (2013.01); *G01R 31/022* (2013.01); *G01R 31/085* (2013.01)

(58) Field of Classification Search
  CPC .......... G01N 17/004; G01N 3/42; G01N 3/16; G01N 3/00; G01R 31/022; G01R 31/085; G01R 31/021

(Continued)

(56) References Cited

U.S. PATENT DOCUMENTS

| 4,435,976 A | 3/1984 | Edward, Jr. ........ 73/83 |
| 5,309,754 A | 5/1994 | Ernst ................ 73/81 |

(Continued)

FOREIGN PATENT DOCUMENTS

| KR | 10-00238895 B1 | 1/2000 |
| KR | 10-2006-0085947 A | 7/2006 |

(Continued)

*Primary Examiner* — Manish S Shah
*Assistant Examiner* — Timothy Graves
(74) *Attorney, Agent, or Firm* — Stein IP, LLC

(57) ABSTRACT

Disclosed is an apparatus for cable inspection, which inspects an aerial cable used in electric power transmission, the apparatus including: first and second plates spaced apart from each other; a lower clamp disposed on the first plate; an upper clamp disposed on the second plate to face the lower clamp and having a through hole in a vertical direction; a distance adjustment unit configured to adjust a separation distance between the first and second plates; an indenter indented in a coating of the cable through the through hole; a first load cell configured to measure an indentation force of the indenter and to output a signal corresponding to the measured indentation force; a second load cell disposed under the lower clamp and configured to measure pressure applied to the cable and to output a signal corresponding to the measured pressure; and an indenter moving unit configured to control movement of the indenter. According to the present invention, deterioration of a cable is measured using a plurality of sensors so that measurement accuracy can be improved and measurement of deterioration of the cable can be performed in a state in which the cable is disposed.

7 Claims, 3 Drawing Sheets

(58) Field of Classification Search
USPC .......................................................... 73/12.09
See application file for complete search history.

(56) References Cited

U.S. PATENT DOCUMENTS

| | | | | |
|---|---|---|---|---|
| 5,677,494 A | * | 10/1997 | Keener | ................. G01N 3/307 |
| | | | | 73/760 |
| 2012/0085155 A1 | * | 4/2012 | Guerout | ................. G01N 3/405 |
| | | | | 73/82 |

FOREIGN PATENT DOCUMENTS

| KR | 10-1161776 B1 | 7/2012 |
|---|---|---|
| KR | 10-1168543 B1 | 7/2012 |

* cited by examiner

APPARATUS FOR CABLE INSPECTION

CROSS-REFERENCE TO RELATED PATENT APPLICATION

This application claims the benefit of Korean Patent Application No. 10-2015-0129615, filed on Sep. 14, 2015, in the Korean Intellectual Property Office, the disclosure of which is incorporated herein in its entirety by reference.

BACKGROUND OF THE INVENTION

1. Field of the Invention

The present invention relates to an apparatus for cable inspection, and more particularly, to an apparatus for cable inspection, which is capable of inspecting an aerial cable in a state in which the aerial cable is disposed.

2. Description of the Related Art

As industries have been developed today, the use of power increases gradually. In addition, facilities are established on a large scale and require high reliability. Thus, stabilization of electric facilities are needed. In particular, high reliability of the supply of electricity may be an essential element for an industrial society.

A cable for supplying power may be classified into an aerial cable and an underground cable. The aerial cable is an electric wire fixed to an insulator installed at a steel tower or telegraph pole. Because the aerial cable is installed at a high position, when an accident occurs, it takes long time to do restoration and thus, accident prevention is preferable.

Thus, it is required that a state of a cable is measured and management of the cable is performed according to the measured state so as to prevent an accident.

A cable exposed to the outside, like the aerial cable, may be deteriorated due to the effect of sun light, etc. In order to check the deterioration state of the cable, part of the installed cable is collected as a sample and is moved to a laboratory and then, deterioration inspection should be carried out. However, sample collecting of the cable inevitably results in damage of the cable.

In addition, a conventional cable indentation testing machine has a structure in which an indentation testing motor operates to apply indentation to a coating of a cable, to measure indentation using one load cell and when an indentation force is equal to or greater than a predetermined indentation force, the indentation testing motor moves backward. Because a single load cell is used in the conventional cable indentation testing machine, the degree of precision is low.

In addition, the conventional cable indentation testing machine has the problem that a cable to be measured is not accurately fixed using a mechanical torque switch, etc. whenever measurement is performed.

In addition, the conventional testing machine has the problem that an error in force measurement occurs due to a change in friction of a driving unit caused by alignment defects during a cable tightening/releasing operation, bending of an indenter caused by repetitive use, etc.

Korean Patent Laid-open Publication No. 2005-100241 may be exemplified as the prior art relating to the present invention.

SUMMARY OF THE INVENTION

The present invention provides an apparatus for cable inspection, which measures deterioration of a cable using a plurality of load cells so that measurement accuracy can be improved.

The present invention also provides an apparatus for cable inspection, which is capable of measurement of deterioration of a cable in a state in which the cable is disposed.

The present invention also provides an apparatus for cable inspection, which induces an accurate close contact by causing fine vibration so that, when a cable is mounted on a clamp, the cable is accurately in close contact with the clamp.

According to an aspect of the present invention, there is provided an apparatus for cable inspection, which inspects an aerial cable used in electric power transmission, the apparatus including: first and second plates spaced apart from each other; a lower clamp disposed on the first plate; an upper clamp disposed on the second plate to face the lower clamp and having a through hole in a vertical direction; a distance adjustment unit configured to adjust a separation distance between the first and second plates; an indenter indented in a coating of the cable through the through hole; a first load cell configured to measure an indentation force of the indenter and to output a signal corresponding to the measured indentation force; a second load cell disposed under the lower clamp and configured to measure pressure applied to the cable and to output a signal corresponding to the measured pressure; and an indenter moving unit configured to control movement of the indenter.

The apparatus may further include a vibrator connected to the lower clamp and configured to apply vibration to the lower clamp.

The apparatus may further include an LM guide disposed between the lower clamp and the second load cell.

Facing surfaces of the upper clamp and the lower clamp may be concavely formed.

The distance adjustment unit may include: a pair of screw bolts configured to connect both ends of the first plate and both ends of the second plate, respectively; a first support load having one end connected to one end of the first plate, the first support load being connected in parallel with the screw bolts; a first motor disposed on one end of the first support load and having a rotational shaft connected to one of the pair of screw bolts; pulleys disposed on one end of each of the pair of screw bolts; and a belt configured to connect the pulleys so as to deliver a rotational force of the first motor to the screw bolt that is not connected to the first motor;

Nuts may be disposed on both ends of each of the first and second plates and are connected to the screw bolts.

The indenter moving unit may include: a second support load disposed on one side of the upper clamp; a second motor fixed to one end of the second support load; a stem nut disposed on a rotational shaft of the second motor; and a bolt having one end connected to an upper portion of the first load cell and the other end coupled to the stem nut and moving in a vertical direction.

The first motor and the second motor may be stepping motors.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

The present invention will now be described more fully with reference to the accompanying drawings, in which exemplary embodiments of the invention are shown.

Figure 1:
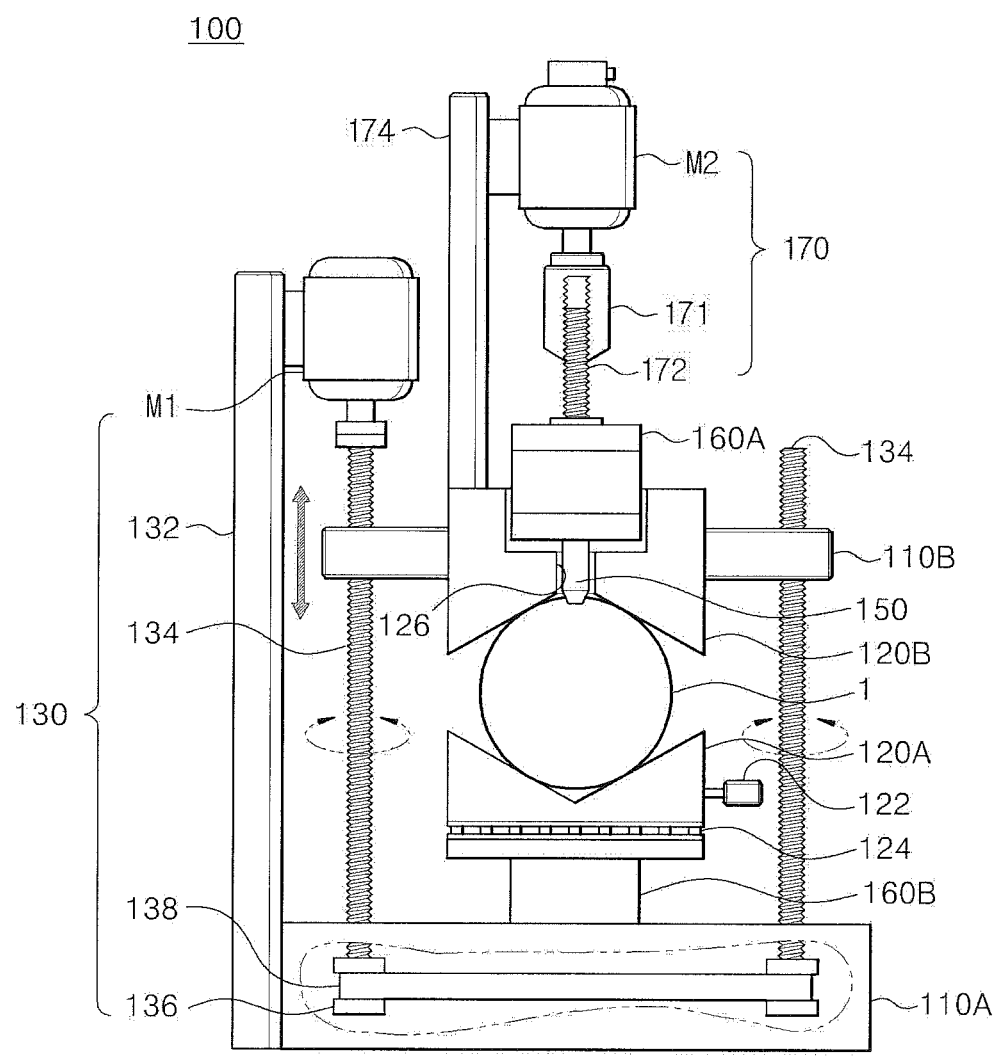
FIG. 1 is a view of an example of a configuration of an apparatus for cable inspection according to an embodiment of the present invention.

FIG. 1 is a view of an example of a configuration of an apparatus for cable inspection according to an embodiment of the present invention.

Referring to FIG. 1, an apparatus 100 for cable inspection according to an embodiment of the present invention includes first and second plates 110A and 110B, a lower clamp 120A, an upper clamp 120B, a distance adjustment unit 130, an indenter 150, a first load cell 160A, a second load cell 160B, and an indenter moving unit 170.

The first and second plates 110A and 110B each have a rectangular shape having a predetermined size and are spaced apart from each other. A separation distance between the first and second plates 110A and 110B may be adjusted by the distance adjustment unit 130 that will be described below.

Elements to be described below are connected to the first and second plates 110A and 110B.

Nut structures are formed on both ends of each of the first and second plates 110A and 110B so that connection of screw bolts 134 that will be described below can be easily performed.

The lower clamp 120A is disposed on the first plate 110A. The lower clamp 120A may fix a cable 1 to be inspected, together with the upper clamp 120B that will be described below.

The upper clamp 120B is disposed on the second plate 110B and faces the lower clamp 120A.

When the cable 1 to be inspected is disposed between the upper clamp 120B and the lower clamp 120A, the upper clamp 120B may fix the cable 1 by reducing a separation distance between the upper clamp 120B and the lower clamp 120A and may maintain a fixed state.

Here, preferably, the lower clamp 120A and the upper clamp 120B are formed in such a way that their facing surfaces are concavely formed and thus fixing of the cable 1 and maintaining of the fixed state can be easily performed.

Preferably, a through hole 126 is formed in the center of the upper clamp 120B in a vertical direction so that the indenter 150 that will be described below may pass through the through hole 126.

Meanwhile, the second load cell 160B that will be described below is disposed under the lower clamp 120A, and a vibrator 122 is connected to one side of the lower clamp 120A.

The vibrator 122 applies predetermined vibration to the lower clamp 120A when the cable 1 to be inspected is disposed between the upper clamp 120B and the lower clamp 120A. That is, when the cable 1 is disposed between the upper clamp 120B and the lower clamp 120A, the cable 1 may deviate from the center of the clamp. In this case, the vibrator 122 applies vibration to the lower clamp 120A, and the lower clamp 120A vibrates in a horizontal direction, and the cable 1 that deviates from the center of the clamp may be disposed in the center of the clamp.

Here, an LM guide 124 may be disposed between the lower clamp 120A and the second load cell 160B that will be described below so that horizontal vibration of the lower clamp 120A can be easily performed.

The LM guide 124 is disposed in parallel with a vibration-applying direction of the vibrator 122 so that, when vibration is applied to the lower clamp 120A, vibration of the lower clamp 120A can be easily performed.

The distance adjustment unit 130 adjusts the separation distance between the first and second plates 110A and 110B. By adjusting the separation distance between the first and second plates 110A and 110B, fixing of the cable 1 may be performed between the lower clamp 120A and the upper clamp 120B.

The distance adjustment unit 130 includes a pair of screw bolts 134, a first support load 132, a first motor M1, pulleys 136, and a belt 138.

The pair of screw bolts 134 are rotated in line with each other so that the separation distance between the first and second plates 110A and 110B may be changed.

One end of each of the pair of screw bolts 134 is connected to both ends of the first plate 110A, and the other end of each of the pair of screw bolts 134 is connected to both ends of the second plate 110B. Here, the pair of screw bolts 134 are disposed in parallel.

Preferably, nuts are disposed on both ends of each of the first plate 110A and the second plate 110B so that connection of the screw bolts 134 can be easily performed.

The first support load 132 is disposed on one end of the first plate 110A perpendicularly to the first plate 110A. In this case, the first support load 132 is disposed in parallel with the screw bolts 134, and a first motor M1 that will be described below is disposed on the first support load 132.

The first motor M1 is disposed on one end of the first support load 132, and a rotational shaft of the first motor M1 is connected to one end of one of the pair of screw bolts 134.

Pulleys 136 are connected to the other end of each of the pair of screw bolts 134. The pulleys 136 are connected to each other via a belt 138. Thus, when the first motor M1 operates, the screw bolt 134 to which the first motor M1 is connected, is rotated, and a rotational force thereof is delivered to the opposite screw bolt 134 via the belt 138 so that the pair of screw bolts 134 may be rotated in line with each other.

Thus, when the pair of screw bolts 134 are rotated in line with each other due to the operation of the first motor M1, the second plate 110B connected to the screw bolt 134 is moved in the vertical direction so that the separation distance between the first and second plates 110A and 110B may be adjusted.

The indenter 150 is moved by the first motor M1 that will be described below in the vertical direction and is indented in the cable 1. The indenter 150 has a shape of a load having a predetermined diameter and a predetermined length.

The indenter 150 is indented in the cable 1 through the through hole 126 on the upper clamp 120B. Moving of the indenter 150 will be described below.

The indenter 150 is a well-known technology in the art and thus, detailed descriptions thereof will be omitted.

The first load cell 160A measures pressure applied when the indenter 150 is indented in the cable 1, measures pressure when the indenter 150 is indented in the cable 1, and outputs a signal corresponding to the measured pressure.

The indenter 150 that will be described below is disposed under the first load cell 160A. Preferably, the first load cell 160A is not rotated around a central axis but is moved only in the vertical direction.

The second load cell 160B is disposed on the first plate 110A, and the lower clamp 120A is disposed above the second load cell 160B. The second load cell 160B measures pressure applied to the lower clamp 120A and outputs a signal corresponding to the measured pressure. Here, because the cable 1 is disposed on the lower clamp 120A, pressure applied to the lower clamp 120A is the same as pressure applied to the cable 1.

A configuration for moving the indenter 150 will now be described.

The indenter moving unit 170 is disposed to move the indenter 150.

The indenter moving unit 170 moves the indenter 150 in the vertical direction so that the indenter 150 may be indented in the cable 1.

The indenter moving unit 170 includes the second support load 174, a second motor M2, a stem nut 171, and a bolt 172.

The second support load 174 is a load having a predetermined length and is disposed on one side of the upper clamp 120B.

The second motor M2 is fixedly disposed on a top end of the second support load 174.

The first motor M1 and the second motor M2 are stepping motors.

The stem nut 171 is connected to a rotational shaft of the second motor M2.

The bolt 172 has a predetermined length. The bolt 172 is disposed on upper portion of the first load cell 160A. The bolt 172 is disposed in parallel with a movement direction of the indenter 150. The bolt 172 is connected to the stem nut 171 and is moved in the vertical direction according to rotation of the stem nut 171.

The bolt 172 having a predetermined length is connected to the stem nut 171. The second load cell 160B that will be described below is connected to a bottom end of the bolt 172, and the indenter 150 is connected to a lower portion of the second load cell 160B.

Thus, when the second motor M2 is rotated in a predetermined direction, a rotational force thereof is delivered to the second load cell 160B that will be described below via the stem nut 171 and the bolt 172 so that the second load cell 160B may be moved in the vertical direction. Because the indenter 150 is connected to a lower portion of the first load cell 160A, the indenter 150 may be indented in the cable 1 in the vertical direction.

The use of the present invention will now be described.

Figure 2:
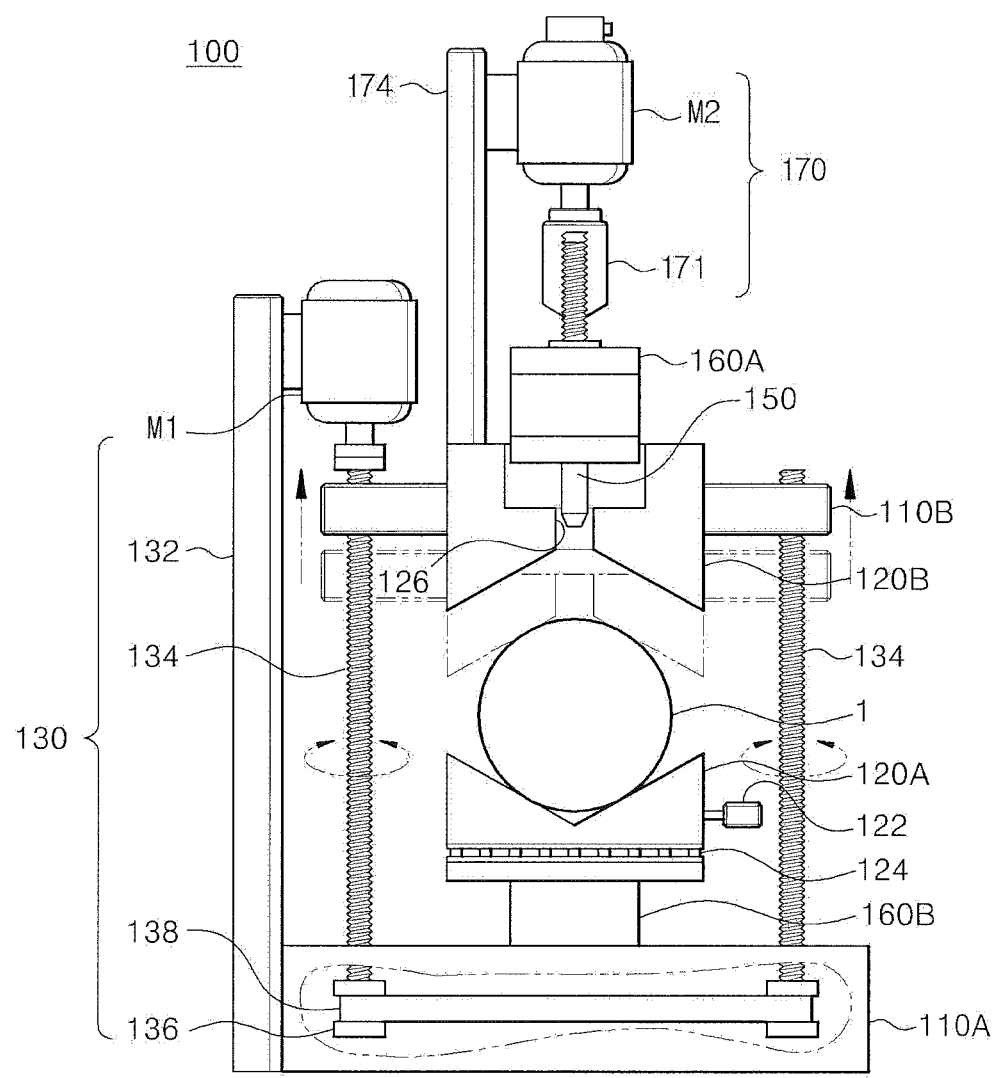
FIGS. 2 and 3 are views illustrating an operating state of the apparatus for cable inspection according to an embodiment of the present invention.
Figure 3:
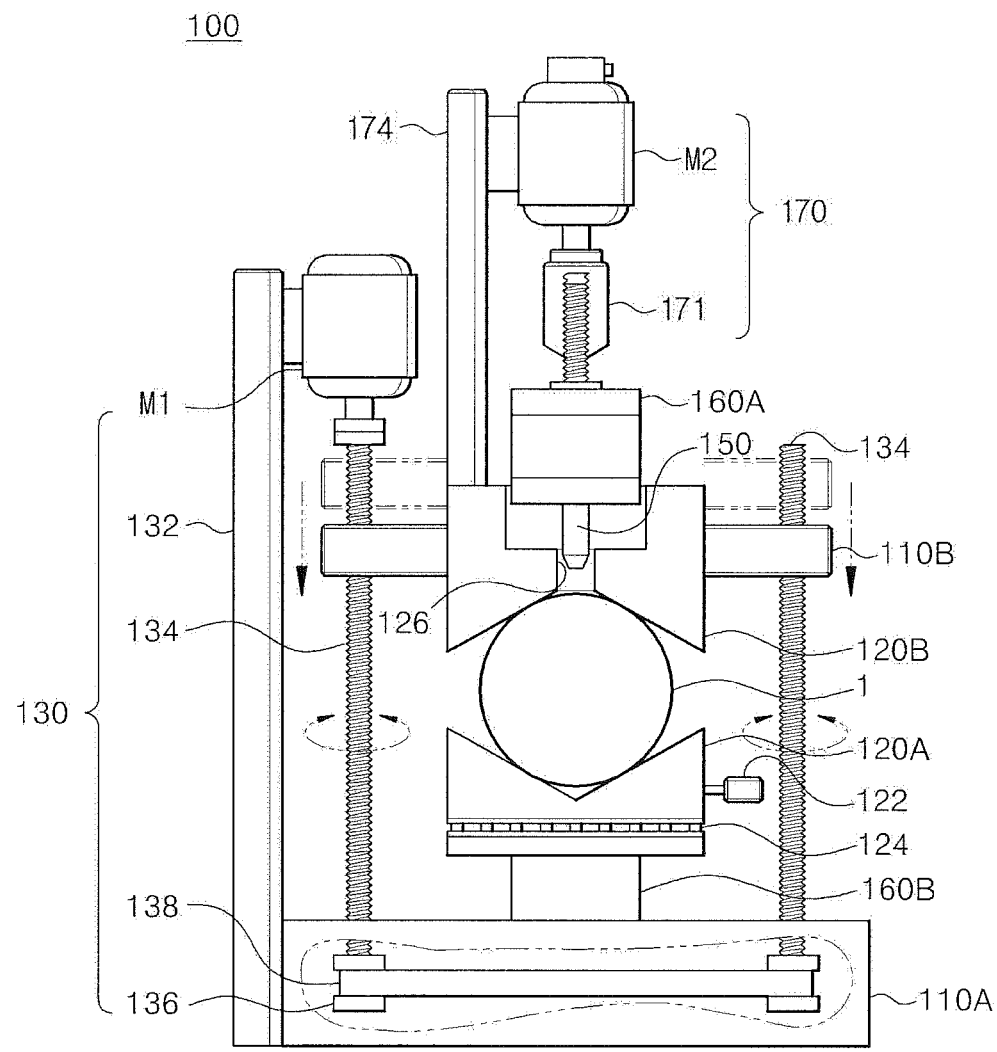

FIGS. 2 and 3 are views illustrating an operating state of the apparatus 100 for cable inspection according to an embodiment of the present invention.

A user carries the apparatus 100 for cable inspection according to the present invention into a position where a cable to be inspected, i.e., an aerial cable is disposed.

Referring to FIG. 2, the user allows the lower clamp 120A and the upper clamp 120B to be spaced apart from each other by a predetermined separation distance so that the cable 1 may be disposed between the lower clamp 120A and the upper clamp 120B. The separation distance in this case is larger than a diameter of the cable 1.

The user disposes the cable 1 between the lower clamp 120A and the upper clamp 120B.

Referring to FIG. 3, the user operates the first motor M1 so that the second plate 110B may be moved in a downward direction. Due to the movement of the second plate 110B, the lower clamp 120A and the upper clamp 120B are in close contact with lower and upper portions of the cable 1 so that the cable 1 may be fixed between the lower clamp 120A and the upper clamp 120B.

When the lower clamp 120A and the upper clamp 120B are in contact with the lower and upper portions of the cable 1, the vibrator 122 operates so that the clamp and the cable 1 may be in close contact with each other.

Subsequently, the user operates the second motor M2 so that the indenter 150 may be indented in the cable 1, as illustrated in FIG. 1.

The user stores signals output from the first load cell 160A and the second load cell 160B in a predetermined storage unit and measures the degree of deterioration of the cable 1 using data output simultaneously with the signals.

According to the present invention, deterioration of a cable is measured using a plurality of sensors so that measurement accuracy can be improved and measurement of deterioration of the cable can be performed in a state in which the cable is disposed.

As described above, according to the present invention, deterioration of a cable is measured using a plurality of sensors so that measurement accuracy can be improved.

In addition, according to the present invention, measurement of deterioration of the cable can be performed in a state in which the cable is disposed.

Furthermore, according to the present invention, fine vibration occurs to induce an accurate close contact so that, when the cable is mounted on a clamp, the cable can be accurately in close contact with the clamp.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An apparatus for cable inspection, which inspects an aerial cable used in electric power transmission, the apparatus comprising:
   first and second plates spaced apart from each other;
   a lower clamp disposed on the first plate;
   an upper clamp disposed on the second plate to face the lower clamp and having a through hole in a vertical direction;
   a distance adjustment unit configured to adjust a separation distance between the first and second plates;
   an indenter indented in a coating of the cable through the through hole;
   a first load cell configured to measure an indentation force of the indenter and to output a signal corresponding to the measured indentation force;
   a second load cell disposed under the lower clamp and configured to measure pressure applied to the cable and to output a signal corresponding to the measured pressure;
   an indenter moving unit configured to control movement of the indenter;
   a vibrator connected to the lower clamp and configured to apply vibration to the lower clamp to force the lower clamp to vibrate in a horizontal direction; and
   an LM guide disposed between the lower clamp and the second load cell.

2. The apparatus of claim 1, wherein facing surfaces of the upper clamp and the lower clamp are concavely formed.

3. The apparatus of claim 1, wherein the distance adjustment unit comprises:
   a pair of screw bolts configured to connect both ends of the first plate and both ends of the second plate, respectively;
   a first support load having one end connected to one end of the first plate, the first support load being connected in parallel with the screw bolts;

a first motor disposed on one end of the first support load and having a rotational shaft connected to one of the pair of screw bolts;

pulleys disposed on one end of each of the pair of screw bolts; and a belt configured to connect the pulleys so as to deliver a rotational force of the first motor to the screw bolt that is not connected to the first motor.

4. The apparatus of claim 3, wherein nuts are disposed on both ends of each of the first and second plates and are connected to the screw bolts.

5. The apparatus of claim 1, wherein the indenter moving unit comprises:

a second support load disposed on one side of the upper clamp;

a second motor fixed to one end of the second support load;

a stem nut disposed on a rotational shaft of the second motor; and a bolt having one end connected to an upper portion of the first load cell and the other end coupled to the stem nut and moving in a vertical direction.

6. The apparatus of claim 5, wherein the first motor and the second motor are stepping motors.

7. The apparatus of claim 1, wherein the vibrator is connected to one side of the lower clamp and configured to apply the vibration to the lower clamp when the cable is disposed between the upper and lower clamps so that any deviation of the cable from the center of the clamps is removed.

* * * * *